United States Patent
Sadek et al.

(10) Patent No.: US 9,011,330 B2
(45) Date of Patent: Apr. 21, 2015

(54) IMPLANTABLE VASCULAR SYSTEM BIOSENSOR WITH GROWN CAPILLARY BEDS AND USES THEREOF

(71) Applicant: California Institute of Technology, Pasadena, CA (US)

(72) Inventors: Akram Sarwat Sadek, Taunton (GB); Axel Scherer, Barnard, VT (US); Muhammad Mujeeb-U-Rahman, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 106 days.

(21) Appl. No.: 13/938,156

(22) Filed: Jul. 9, 2013

(65) Prior Publication Data

US 2014/0012122 A1     Jan. 9, 2014

Related U.S. Application Data

(60) Provisional application No. 61/669,553, filed on Jul. 9, 2012.

(51) Int. Cl.
| | |
|---|---|
| *A61B 5/00* | (2006.01) |
| *A61B 5/1455* | (2006.01) |
| *A61B 5/1486* | (2006.01) |
| *A61B 5/145* | (2006.01) |
| *A61B 5/1459* | (2006.01) |
| *A61B 5/1473* | (2006.01) |

(52) U.S. Cl.
CPC .............. *A61B 5/6846* (2013.01); *A61B 5/686* (2013.01); *A61B 5/6876* (2013.01); *A61B 5/14503* (2013.01); *A61B 5/1459* (2013.01); *A61B 5/1473* (2013.01); *A61B 5/14865* (2013.01); *A61B 2562/028* (2013.01); *A61B 2562/14* (2013.01); *A61B 2562/164* (2013.01)

(58) Field of Classification Search
CPC ............. A61B 5/14503; A61B 5/1455; A61B 5/14551; A61B 5/14552; A61B 5/6846; A61B 5/1473; A61B 5/1486; A61B 5/686; A61B 2562/166
USPC .................. 600/309, 310, 344, 345, 347, 348
See application file for complete search history.

(56) References Cited

U.S. PATENT DOCUMENTS

| | | | |
|---|---|---|---|
| 6,304,766 B1 * | 10/2001 | Colvin, Jr. ..................... 600/317 |
| 6,442,413 B1 * | 8/2002 | Silver ............................. 600/345 |
| 6,466,810 B1 * | 10/2002 | Ward et al. .................... 600/345 |
| 7,736,309 B2 * | 6/2010 | Miller et al. .................. 600/300 |
| 8,024,020 B2 * | 9/2011 | Rosero ........................... 600/310 |

(Continued)

OTHER PUBLICATIONS

ISR for PCT/US2013/049799, 14 pages.

(Continued)

*Primary Examiner* — Eric Winakur
(74) *Attorney, Agent, or Firm* — Hema Vakharia-Rao; Nixon Peabody LLP

(57) ABSTRACT

An implantable biocompatible biosensor is described herein. The biosensor includes a chip layer including a plurality of holes fabricated vertically there through, a power source, one or more sensors on the chip layer and coupled to the power source and a hydrogel matrix including one or more angiogenesis stimulating factors in contact with the chip layer. The stimulating factors stimulate growth of organic material through the plurality of holes when the biosensor is implanted in a subject.

24 Claims, 4 Drawing Sheets

(56) References Cited

U.S. PATENT DOCUMENTS

| | | |
|---|---|---|
| 2006/0008500 A1 | 1/2006 | Chavan et al. |
| 2007/0184222 A1 | 8/2007 | Delouise et al. |
| 2008/0154101 A1 | 6/2008 | Jain et al. |
| 2008/0228054 A1 | 9/2008 | Shults et al. |
| 2010/0160760 A1 | 6/2010 | Shults et al. |

OTHER PUBLICATIONS

Written Opinion for PCT/US2013/049799, 6 pages.

* cited by examiner

IMPLANTABLE VASCULAR SYSTEM BIOSENSOR WITH GROWN CAPILLARY BEDS AND USES THEREOF

CROSS-REFERENCE TO RELATED APPLICATIONS

This application claims priority from U.S. Provisional Patent Application No. 61/669,553, filed on Jul. 9, 2012, which is incorporated herein by reference in its entirety.

GOVERNMENT RIGHTS

This invention was made with government support under W911NF-07-1-0277 awarded by the Army Research Office. The government has certain rights in the invention.

TECHNICAL FIELD

This invention relates to implantable biocompatible biosensors that include a matrix having angiogenesis stimulating factors to stimulate growth of a capillary bed through the biosensor and to detect analytes in, for example, blood.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

There is a need for wireless, implantable sensors that can detect the concentrations of various proteins, metabolites and ions in blood in real-time. Direct implantation of biosensors within tissue does not facilitate such detection, as it relies on the diffusion of molecules from the blood to the interstitial fluid to the sensor. This diffusion process takes substantial time due to the distance between the blood to the sensor. There is thus a delay of tens of minutes to hours between the variations in concentration of target analytes in the blood and that detected by the sensors. Furthermore, the eventual encapsulation of implanted devices within a thick layer of fibrous tissue due to tissue reaction further impedes the diffusion of such molecules to onboard sensors.

The invention described herein presents a technique for interfacing a sensor chip directly with the vascular system to allow real-time detection of species in blood, through the formation of a capillary bed within the chip. As a result, diffusion of target molecules in blood to the sensors occurs at the same physiological length scale as that from blood in capillaries to the tissue they supply in the body.

SUMMARY

A multilayer chip, embedding microelectrodes and/or other micro/nano sensors (such as nanoelectromechanical systems, optical resonators etc.) within a gelatinous matrix is disclosed. Micromachined capillary holes 20-50 um in diameter are fabricated vertically throughout the chip and are also filled with the matrix which encourages growth of a capillary bed. The holes are spaced apart similarly to the dimension of the hole diameter. The area for exchange between the capillary bed and sensors is determined by the number of sensor matrix layers in the chip, and the number of capillary holes in the chip. The chip can alternatively consist of one layer, incorporating the sensor electronics, power and communication systems. The number of capillary holes is scaled up to increase diffusional exchange with the molecules. Real-time detection is ensured as long as every part of the biosensor matrix is within 10-20 μm of a capillary. Transverse channels may be etched in between the chip layers, which branch off the vertical through holes. The channels guide capillary growth between two chip layers and allow on-chip spectroscopic blood measurement to be performed. One chip layer may contain a light-emitting diode (LED) or a vertical cavity surface emission laser (VCSEL). The second layer includes an integrated series of photodetectors with spectral filters. Absorption or fluorescence within the bloodstream is detected by the photodetectors as the VCSEL or LED illuminates the blood vessel.

BRIEF DESCRIPTION OF THE FIGURES

Exemplary embodiments are illustrated in the referenced figures. It is intended that the embodiments and figures disclosed herein are to be considered illustrative rather than restrictive.

DETAILED DESCRIPTION OF THE INVENTION

Figure 1:
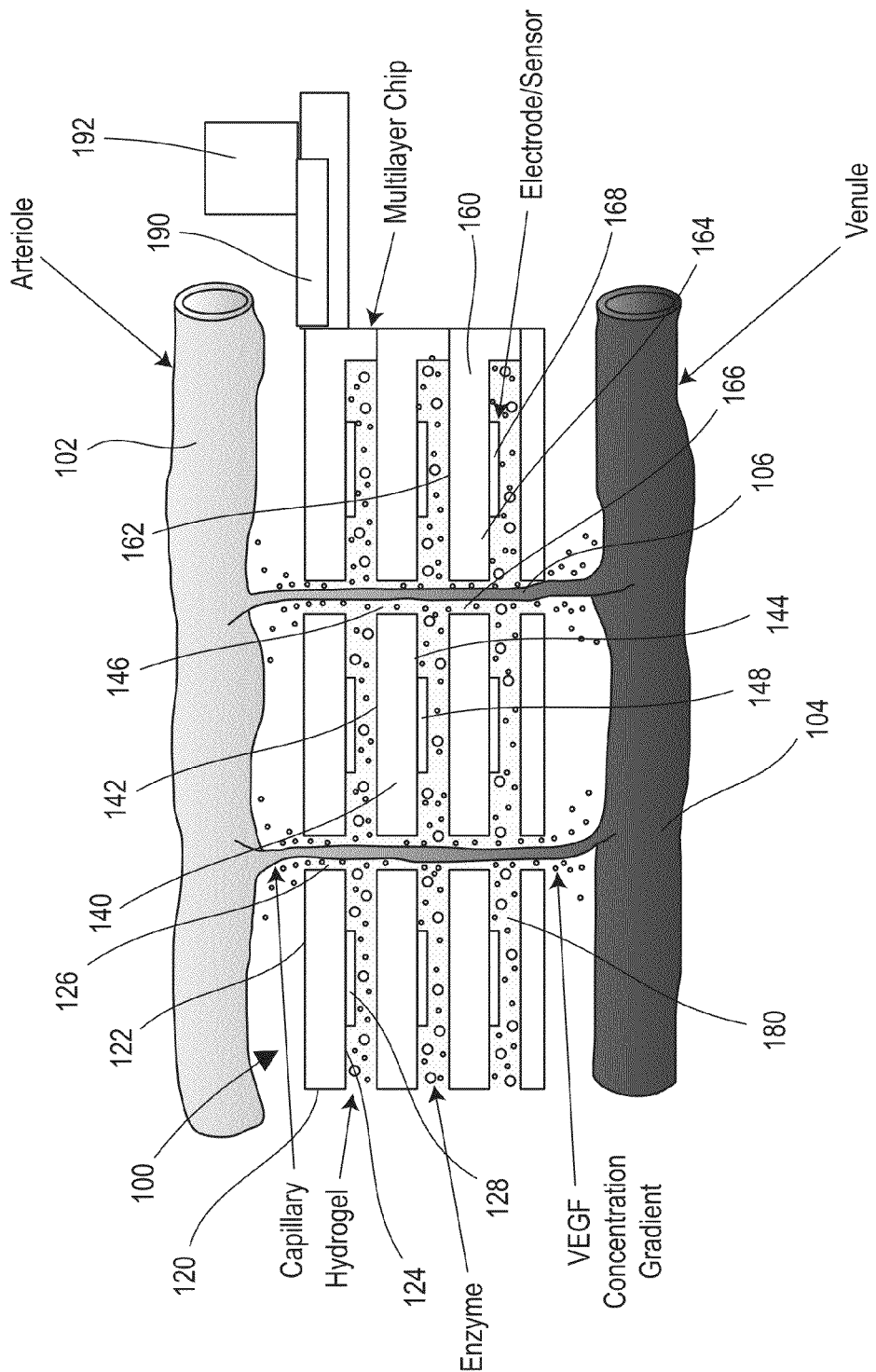
FIG. 1 is a cross-section view of a biosensor having a multilayer interface with grown blood vessels.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the examples described. Indeed, the examples are in no way limited to the methods and materials described.

To overcome the problem of sensing from blood, described herein is a device that interfaces with the vasculature in the same manner as the tissue itself interfaces with the vasculature. Instead of placing the sensor within the blood proper via the lumen of a blood vessel, which would elicit thrombosis, the device described herein induces the body to bring the vasculature to the chip through the formation of a capillary bed via angiogenesis.

The circulatory system consists of the heart, lungs and a system of arteries and arterioles that supply oxygenated blood to the tissues via the capillary bed. A capillary lumen is only about 10 μm in diameter, and a capillary exists within a few tens of microns of every cell in the body. This ensures oxygen and nutrients in the blood can quickly diffuse to the cells through the capillary walls, which are only one cell diameter thick. Likewise, carbon dioxide and waste products diffuse from the tissue into the blood for removal via the capillary bed. The capillaries then return the blood to the heart via a system of venules and veins. The blood itself never comes into contact with any tissue in the body except for the specialized endothelial cells which line the lumen of every blood vessel, and from which the capillaries are solely comprised.

Interfacing with the blood stream may be accomplished by building a capillary bed around a micro/nanostructured biosensor, allowing diffusional exchange of species with the sensor.

An implantable biocompatible biosensor is described below. In one embodiment, the biosensor has a single layer chip having a chip layer and a hydrogel matrix layer. In another embodiment, the biosensor includes a multilayer chip having two or more chip layers and two or more hydrogel matrix layers. Each chip layer includes a plurality of micromachined holes fabricated vertically through the chip. In a multi-layer biosensor, the pluralities of holes are aligned between each of the chip layers. The hydrogel matrix includes one or more angiogenesis stimulating factors, resulting in growth of organic material (for example, capillary beds) through the plurality of holes in the chip when the biosensor is implanted in a subject. The chip layers further include a power source and one or more sensors. The sensors on the chip layers are coupled to the power source. The chip layers further include one or more transmitters in communication with sensors. The sensors transmit a signal representative of a sensed characteristic (for example, an analyte) present in the grown organic material (such as a capillary bed). The transmitter converts the signal from the sensor into a digital signal representative of the sensed analyte and transmits the digital signal to a receiver outside the body. The signal received by the receiver may be processed by a processor or analyzer.

Another example is an implantable biocompatible biosensor having a first chip layer having a vertical hole between a top surface and a bottom surface, a power source, one or more sensors fabricated on the top surface, a channel fabricated substantially perpendicular to the vertical hole on the bottom surface and a hydrogel matrix having one or more angiogenesis stimulating factors filling the hole and the channel. The hydrogel matrix stimulates growth of organic material when the biosensor is implanted in a subject. The sensor may further include a second chip layer having a hole in alignment with the hole of the first chip layer, wherein the sensor includes a laser and a photodiode on the second chip layer, the second chip layer located under the first chip layer and the hydrogel matrix filling the space between the first and second chip layers. The chip layers further include one or more transmitters in communication with sensors. The sensors transmit a signal representative of a sensed characteristic (for example, an analyte) present in the grown organic material (such as a capillary bed). The transmitter converts the signal from the sensor into a digital signal representative of the sensed analyte and transmits the digital signal to a receiver outside the body. The signal received by the receiver may be processed by a processor or analyzer.

Another example is a system for assaying concentrations of proteins, metabolites and ions in the blood. The system includes an implantable biocompatible biosensor having a chip comprising a power source for the biosensor, one or more sensors, a transmitter in communication with the sensor for converting the signal from the sensor into a digital signal and micro-machined holes fabricated vertically throughout the chip, and a hydrogel matrix having one or more angiogenesis stimulating factors filling the hole. The hydrogel matrix stimulating growth of organic material when the biosensor is implanted in a subject. The system may include an external excitation light source (for example, an LED). The system may also include an external receiver to receive the digital signal transmitted by the transmitter and a processor or analyzer to process the signal received by the receiver.

Also described herein is a method for interfacing an implantable biocompatible biosensor with the vascular system in a subject. The method includes providing a biosensor described herein and implanting the biosensor in the subject so as to create a capillary bed through the plurality of holes and channels in proximity to the sensor. The method further includes detecting the analyte from the capillary bed via the sensor.

Also described herein are methods for detecting an analyte in a subject in need thereof. The method includes providing a biosensor described herein and implanting the biosensor to grow organic material (for example, capillary beds) in the matrix, wherein the biosensor detects the level of one or more analytes in the grown organic material, converting the detected level of the one or more analytes from the sensor into an electrical signal and transmitting the signal to an external detector to provide data relating to the detected analyte level.

In some embodiments, the biosensors described herein may be implanted in areas such as the earlobe, areolar layer of the skin over the wrist, arm, or other appendage, or within the dermis layer of the nail bed.

FIG. 1 is a cross-section view of a biosensor 100 having a multilayer interface with grown blood vessels. The biosensor 100 is implanted in a subject for the purpose of measuring a physical parameter in real-time from blood. The biosensor 100 is implanted in the subject in areas where an arteriole 102 and a venule 104 are present. Blood flows between the arteriole 102 and the venule 104 as explained above. A capillary bed 106 is grown between the arteriole 102 and the venule 104.

The biosensor 100 includes a first chip layer 120 having a top surface 122 in proximity to the arteriole 102 and an opposite bottom surface 124. The first layer 120 includes a plurality of holes 126 drilled therethrough. The bottom surface 124 includes a plurality of electrodes 128 that compose a sensor array. The electrodes 128 are in proximity to the plurality of holes 126.

The biosensor 100 includes a second chip layer 140 having a top surface 142 in proximity to the bottom surface 124 of the first chip layer 120 and an opposite bottom surface 144. The second layer 140 includes a plurality of holes 146 drilled therethrough. The bottom surface 144 includes a plurality of electrodes 148 that compose a sensor array. The electrodes 148 are in proximity to the plurality of holes 146.

The biosensor 100 includes a third chip layer 160 having a top surface 162 in proximity to the bottom surface 144 of the second chip layer 140 and an opposite bottom surface 164. The third layer 160 includes a plurality of holes 166 drilled therethrough. The bottom surface 164 includes a plurality of electrodes 168 that compose a sensor array. The electrodes 168 are in proximity to the plurality of holes 166. The bottom surface 164 is in proximity to the existing venule 104.

A hydrogel matrix 180 is formed between the chip layers 120, 140 and 160 and in the respective plurality of holes 126, 146 and 166. Each of the plurality of holes 126, 146 and 166 for the respective chip layers 120, 140 and 160 are in substantial alignment with each other. In this example, the holes 126, 146 and 166 may have a diameter in the range of any one or more of 10-100 µm, 20-80 µm, 30-70 µm, 40-60 µm, 30-40

μm, 30-50 μm, 30-60 μm or a combination thereof. The spacing between each of the holes 126, 146 and 166 on each of the chip layers 120, 140 and 160 may be the same as the diameter of each hole.

The hydrogel matrix 180 includes one or more angiogenesis stimulating factors which promotes the growth of the capillary bed 106 through the plurality of holes 126, 146 and 166. In this example, the hydrogel matrix 180 incorporates a vascular endothelial growth factor (VEGF). Once the biosensor 100 is implanted into tissue, the VEGF concentration gradient from diffusion out of the hydrogel matrix 180 induces arterioles and capillaries such as the arteriole 102 to branch off existing vasculature and guide capillaries to grow between the chip layers 120, 140 and 160. The hydrogel matrix 180 also acts like a tissue to absorb species that diffuse from the capillaries that incorporate throughout the biosensor 100. Once the capillary bed 106 has been grown, diffusional exchange occurs between the capillaries and the sensor array of electrodes 128, 148 and 168 in the biosensor via the hydrogel matrix 180. This buffering ameliorates transient noise in the signals from the electrodes 128, 148 and 168. The hydrogel matrix 180 may also incorporate biosensing molecules/proteins that, on binding the primary species of interest, produce secondary species that can be detected by the on-chip sensors such as the electrodes 128, 148 and 168.

The growth of the capillary bed 106 through the plurality of holes 126, 146 and 166 brings the blood flow of the subject in proximity to the electrodes 128, 148 and 168 providing real-time sensing of the blood. Upon contact of an analyte with the electrodes 128, 148 and 168, an enzyme-catalyzed reaction, or antigen-antibody reaction, or ligand-receptor reaction may be used to create a measurable change in a physical parameters detected by the electrodes 128, 148 and 168. The physical parameter may be a densitometric, refractometric, calorimetric, electrical, or chemical parameter.

Each of the electrodes 128, 148 and 168 are coupled to a controller 190. The controller 190 is coupled to a power source such as a photovoltaic cell or radiofrequency coil 192. The power source provides electrical power to the electrodes 128, 148 and 168 and the controller 190. The controller 190 which digitizes signals from the electrodes 128, 148 and 168. The controller 190 also includes a transmitter which sends the signals to an external receiver. This transmitter may be optical, such as a VCSEL or other micro laser, or may be radiofrequency, such as a microwave transmitting coil.

Of course it is to be understood there may be fewer or more layers such as the chip layers 120, 140 and 160 in a biosensor as that shown in FIG. 1. The number of chip layers is a design preference.

Figure 2:
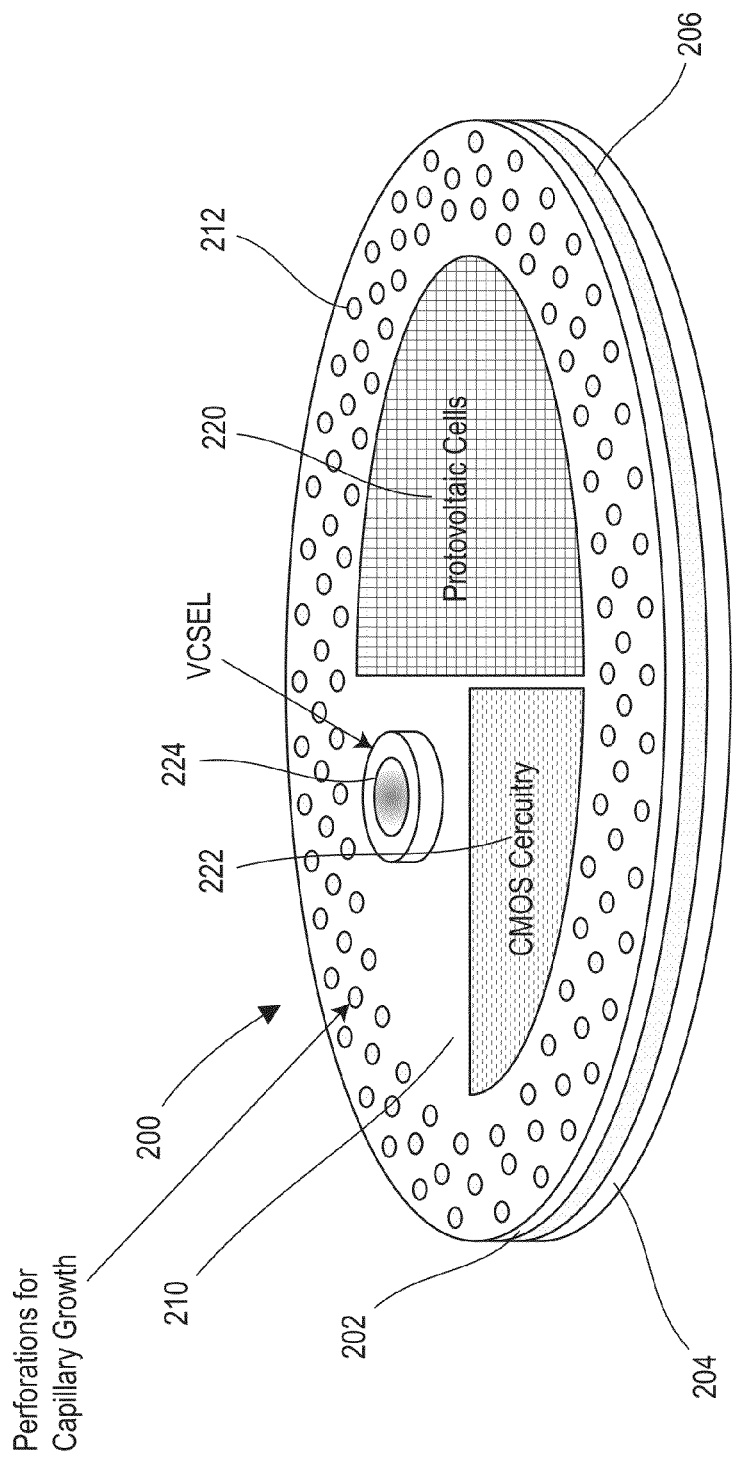
FIG. 2 is a perspective view of a single layer biosensor incorporating electronics, communication and power on the layer.

FIG. 2 is a perspective view of a single layer biosensor 200 incorporating electronics, optical communication and photovoltaic powering for implantation in a subject and circulatory system interfacing. The biosensor 200 is implanted in the subject and allows for the growth of a capillary bed through the biosensor 200 for real-time measurement for a characteristic or an analyte in the blood of the subject. The biosensor 200 includes a top circular chip 202 and a bottom circular chip 204. A hydrogel matrix 206 is applied between the circular chips 202 and 204.

The top circular chip 202 has a top surface 210 that includes a plurality of holes 212 drilled through the chip 202. The plurality of holes 212 are located on the perimeter of the top surface 210. The plurality of holes 212 have corresponding holes (not shown) drilled through the bottom chip 204.

The top surface 210 includes a photo-voltaic array 220 which provides power to sensor circuitry on a circuit area 222. The circuit area 222 includes a controller, a transmitter and sensor circuits. The sensors are located near the holes. The transmitter in the circuitry 222 is coupled to a vertical cavity surface emitting laser (VCSEL) 224 for optical data transmission. The VCSEL 224 may be replaced by any laser diode such as double heterostructure lasers, quantum well lasers, quantum cascade lasers, separate confinement heterostructure lasers, distributed feedback lasers, vertical external cavity surface emitting lasers (VCSELs) or external-cavity diode lasers.

The hydrogel matrix 206 allows the growth of a capillary bed through the holes 212.

Figure 3:
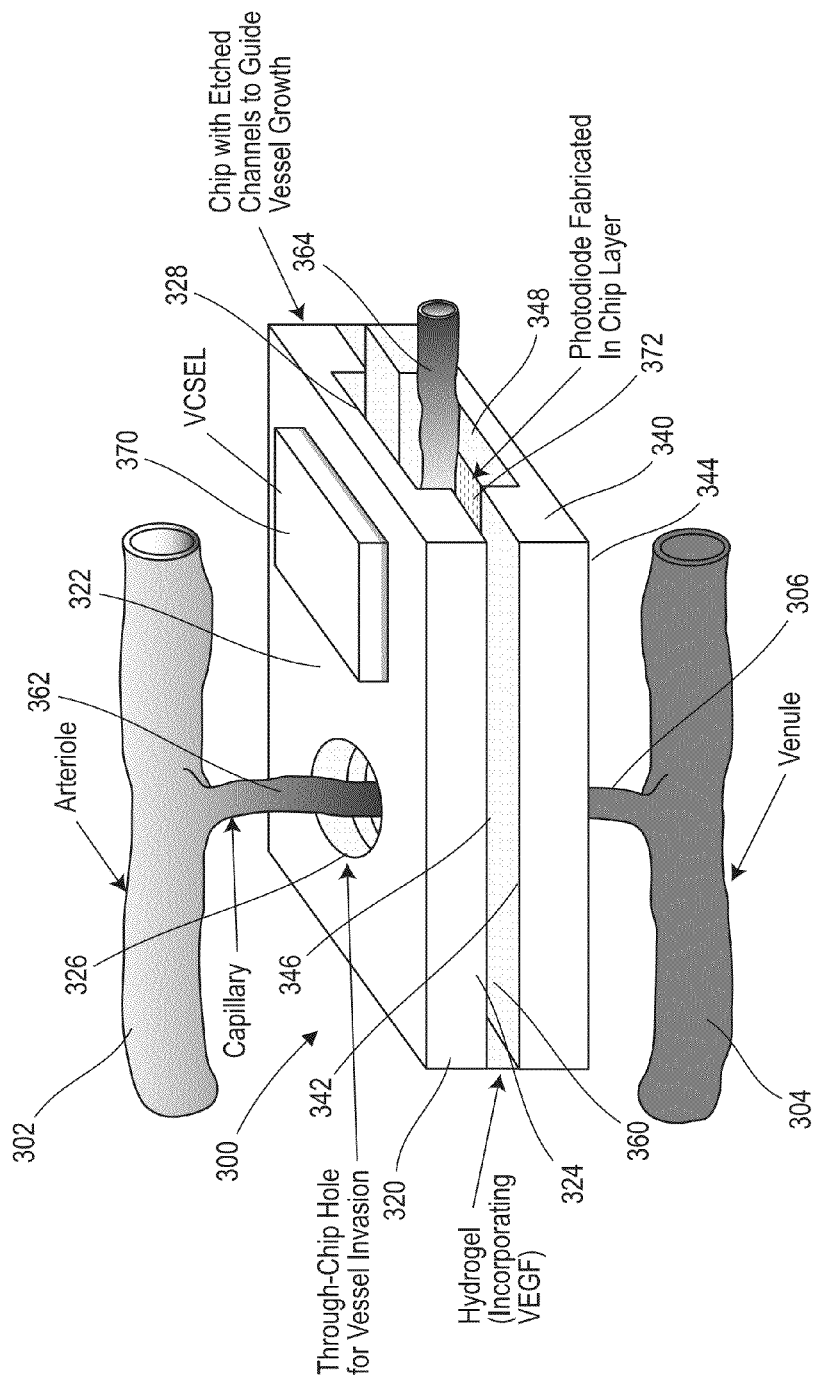
FIG. 3 is a close up perspective view of an example angiogenesis sensor that performs blood spectroscopic measurements.

FIG. 3 is a close up perspective view of an angiogenesis sensor 300 that performs blood spectroscopic measurements. The biosensor 300 is implanted in a subject for the purpose of measuring a characteristic in real-time from blood. The biosensor 300 is implanted in a subject for the purpose of measuring a physical parameter in real-time from blood. The biosensor 300 is implanted in the subject in areas where arteriole 302 and venule 304 are present. Blood flows between the arteriole 302 and the venule 304 as explained above. A capillary bed 306 is grown between the arteriole 302 and the venule 304.

The biosensor 300 includes an arteriole side chip layer 320 having a top surface 322 in proximity to the arteriole 102 and an opposite bottom surface 324. The first layer 320 includes a plurality of holes such as a hole 326 drilled therethrough. The bottom surface 324 includes a lateral channel 328 that is formed substantially perpendicularly to the orientation of the hole 326.

The biosensor 300 includes a venule side chip layer 340 having a top surface 342 in proximity and facing the bottom surface 324 of the chip layer 320 and an opposite bottom surface 344. The chip layer 340 includes a plurality of holes such as a hole 346 drilled therethrough. As shown in FIG. 3, the holes in the chip layers 320 and 340 are in alignment with each other. The top surface 342 includes a lateral channel 348 that is formed substantially perpendicularly to the orientation of the hole 346.

A hydrogel matrix 360 is formed between the chip layers 320 and 340, in the holes 326 and 346 and the channels 328 and 348. The hydrogel matrix 360 includes one or more angiogenesis stimulating factors, which promote the growth of the capillary bed 306 in the form of a capillary 362 grown through the holes 326 and 346. Another capillary 364 is grown through the channels 328 and 348. The interspacing of capillaries such as the capillaries 362 and 364 allows real-time sensing of the characteristics of the blood by the sensor 300.

A VCSEL 370 is fabricated on the top surface 322 of the chip 320. The VCSEL 370 emits light, which is absorbed by the capillary 364 in the channels 328 and 348. The VCSEL 370 may be replaced by any laser diode such as double heterostructure lasers, quantum well lasers, quantum cascade lasers, separate confinement heterostructure lasers, distributed feedback lasers, vertical external cavity surface emitting lasers (VCSELs) or external-cavity diode lasers. The absorbed light is detected by a photo-detector 372 which is located on the top layer 342 of the chip layer 340. The photo-detector 372 in this example is a photo-diode which emits an electrical signal indicative of the detected light which is representative of an analyte in the blood. As will be explained below, a spectral filter may be fabricated with the photo-detector 372 in order to detect light from specific wavelengths for purposes of measuring different analytes.

Figure 4:
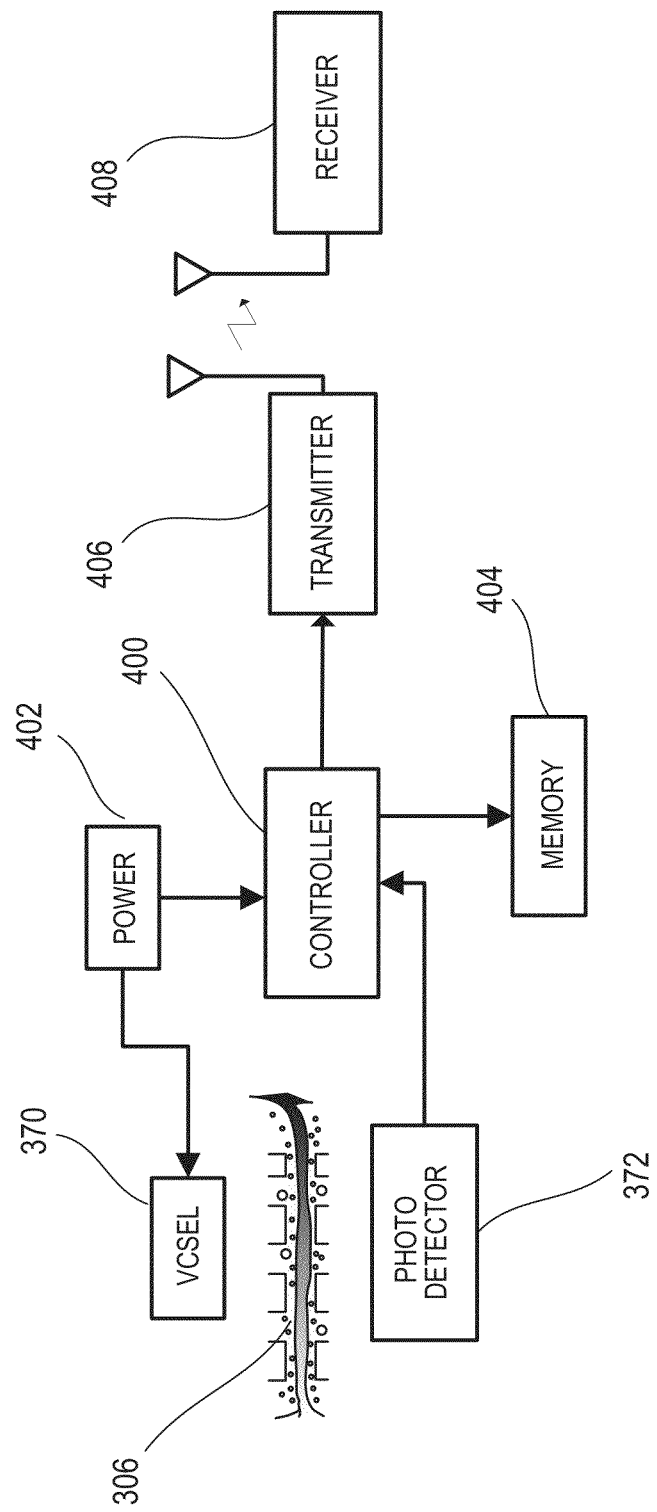
FIG. 4 shows a circuit diagram of the electronics for the single layer biosensor chip in FIG. 3.

FIG. 4 is a circuit diagram of the sensor circuit for the biosensor 300 in FIG. 3. A similar circuit may be used for the electrode sensors of the biosensor 100 in FIG. 1 or biosensor 200 in FIG. 2. The components shown in FIG. 4 may be fabricated in either chip layer 320 or 340 in FIG. 3. As explained above, the VCSEL 370 emits light through blood carried by the capillary bed 306 which grows in hydrogel matrix near the photo-detector 372.

It is to be understood that the biosensor 300 in FIG. 3 may be one of an array of sensors or a singular sensor coupled to a controller 400. The output of the photo-detector 372 is an analog signal that is representative of the level of light detected through the blood from the output of the VCSEL 370. A power source 402 such as a non-rechargeable battery, radiofrequency coil or a photovoltaic cell powers the VCSEL 370 and the controller 400. The controller 400 includes an analog to digital converter, which converts the received signal from the photo-detector 372 to a digital signal. The controller 400 is coupled to an internal memory 404 which may include programming instructions for the controller 400, initial parameters and intermediate storage for detected values. The controller 400 is coupled to a transmitter 406. The controller 400 outputs a digital signal to the transmitter 406 which is representative of the detected light by the photo-detector 372. The transmitter 406 sends a wireless signal to an external receiver 408. This signal may be optical, such as that from a VCSEL or other micro laser, or may be radiofrequency, such as from a microwave transmitting coil. The external receiver 408 is external to the subject and may be coupled to additional electronics to analyze the measurements from the biosensor 300.

The hydrogel matrix fills each of the plurality of holes in each of the chip layers. In some embodiments, the hydrogel matrix is bovine serum albumin (BSA)-based, agarose-based, polyethylene glycol (PEG)-based, polyethylene oxide (PEO)-based, polyvinyl alcohol (PVA)-based, polyacrylic acid (PAA)-based, poly propylene furmarate-co-ethylene glycol (P(PF-co-EG))-based, alginate-based, chitosan-based, collagen-based, fibrin-based, gelatin-based, hyaluronic acid (HA)-based, poly 2-hydroxyethyl methacrylate (PHEMA)-based, poly carboxybetaine methacrylate (PCBMA)-based or a combination thereof. The use of an appropriate biocompatible hydrogel matrix would be apparent to one skilled in the art. The hydrogel matrix incorporates one or more angiogenesis stimulating factors. Once the chip is implanted into tissue, the angiogenesis stimulating factor concentration gradient diffuses out of the hydrogel and induces, for example, the arterioles and capillaries to branch off existing vasculature and guide capillaries to grow into the chip. The hydrogel matrix also acts like a tissue, in the sense of a buffer to absorb species that diffuse from the capillaries that incorporate throughout the chip. Once the capillary bed has been established, diffusional exchange occurs between the capillaries and the sensor array in the chip via the gel matrix. This buffering ameliorates transient noise in the signal. The hydrogel matrix may also incorporate biosensing molecules/proteins (including but not limited to enzymes, antibodies, antigens and catalysts) that, on binding the primary analytes of interest, produce secondary species that can be detected by the on-chip electronic sensors.

As described herein, the hydrogel matrix fills the channel and plurality of holes in each of the chip layer and forms a layer between each of the chip layers. The angiogenesis stimulating factors in the matrix stimulate the formation of arterioles and capillaries through the holes and the channel. As blood flows through the newly formed arterioles and capillaries, the analytes from the blood diffuse into and are absorbed by the matrix and are detected by the sensor. In addition to angiogenesis stimulating factors, the hydrogel matrix may also include agents that react with the analytes that have diffused into the matrix from the blood flowing through the arterioles and capillaries. The sensors may also detect the analytes bound to the agents.

The angiogenesis stimulating factors include but are not limited to any one or more of vascular endothelial growth factor (VEGF), fibroblast growth factor (FGF)-1, FGF-2, platelet derived growth factor (PDGF), transforming growth factor (TGF)-β, angiopoietins, matrix metalloproteinase (MMP) or a variant, mutant or peptidomimetic thereof, or a combination thereof.

In some embodiments, the sensor in the various biosensors described herein is any one or more of an electrode, a nano-electromechanical sensor, a micro/nanoscale field effect transistor (FET), an optical resonator or a combination thereof. In some embodiments, the sensors may be additionally functionalized with any one or more of DNA/RNA aptamers, antibodies for specific proteins, enzymes, ligands or a combination thereof.

In various embodiments, one or more sensors detect one or more metabolite levels for diagnosing, prognosticating or monitoring metabolic disorders. Examples of metabolic disorders include, but are not limited to diabetes, phenylketonuria (PKU), acid lipase disease, Barth syndrome (BTHS), central pontine myelinolysis, disorders of amino acid metabolism, disorders of carbohydrate metabolism, disorders of lipid metabolism, Farber's disease, G6PD deficiency (Glucose-6-Phosphate Dehydrogenase), gangliosidoses, Hunter syndrome, trimethylaminuria, Lesch-Nyhan syndrome, lipid storage diseases, metabolic diseases of muscle, metabolic myopathies, mitochondrial myopathies, mucolipidoses, mucopolysaccharidoses, Pompe disease, Type I glycogen storage disease, urea cycle disease, urea cycle disorder, hyperoxaluria and oxalosis.

In various embodiments, one or more sensors detect one or more antigens for diagnosing, prognosticating or monitoring infectious diseases such as viral infection, bacterial infection, and fungal infection.

In various embodiments, one or more sensors detect one or more chemicals for diagnosing, prognosticating or monitoring intoxication or attacks from biological chemical weapons.

In various embodiments, one or more sensors detect one or more autoantibodies or inflammatory molecules for diagnosing, prognosticating or monitoring inflammatory disorder, autoimmune disease, arthritis, multiple sclerosis, inflammatory bowel disease, and Crohn's disease.

In various embodiments, one or more sensors detect one or more neurotransmitters for diagnosing, prognosticating or monitoring neurological disorders, depression (insufficient serotonin), Parkinson's disease (insufficient dopamine), psychoses (excessive dopamine), and epilepsy.

In various embodiments, one or more sensors detect one or more oxygen levels or tumor biomarkers for diagnosing, prognosticating or monitoring brain tumors, prostate cancer, and tumor growth and aggressiveness.

In various embodiments, one or more sensors detect one or more hormone levels for diagnosing, prognosticating or monitoring hormonal disorder or imbalance, pregnancy and term, polycystic ovarian syndrome (PCOS), thyroid dysfunction, hypothyroidism, hyperthyroidism, and adrenal fatigue.

In various embodiments, one or more sensors detect one or more oxygen levels, blood flow rate and volume for diagnosing, prognosticating or monitoring cardiovascular disease.

In various embodiments, one or more sensors detect one or more blood proteins including, but not limited to, heart-type fatty acid-binging protein (H-FABP) and troponin I (TnI) for diagnosing, prognosticating or monitoring cardiovascular disease.

Analytes in blood that may be detected by the biosensors described herein include but are not limited to Hemoglobin, Albumin, Globulins Complement Proteins, Fribrinogen, Lipids, Fatty Acids, Phospholipids, Cholesterol, Triodothyronine, Triglyceriedes, Glucose, Non-protein Nitrogen, Ceruloplasmin, Protoporphyrin, Glutathione, Prealbumin, Salicylates, Urea Nitrogen, Lactate (Lactic Acid), Base, Sodium, Chloride, Carbon Dioxide, Oxygen, Bicarbonate, Potassium, Alpha Amino Acid Nitrogen, Amino Acids, Phosphorus, Calcium. Other analytes in tissues and organs include ATP, NADPH, creatine, and creatinine.

Analytes can be detected by sensors in the example devices based on their contact to the sensor such as the electrodes 128, 148 and 168 in FIG. 1. Enzymatic-Chemical, electrochemical, piezoelectric, thermoelectric, surface plasmon resonance, surface acoustic wave, optical absorbance, and/or optical rotation of polarized light sensors may be used to detect the contact and hence the analytes. For example, upon contact of an analyte with the sensor, an enzyme-catalyzed reaction, or antigen-antibody reaction, or ligand-receptor reaction may be used to create a measurable change in a physical parameters detected by the sensor. The physical parameter may be a densitometric, refractometric, calorimetric, electrical, or chemical parameter. For example, if glucose is the analyte, the biosensor of the invention may incorporate an enzyme that selectively reacts with glucose, such as glucose oxidase (GOD), hexokinase, glucose-6-phosphate dehydrogenase (G-6-PD), or glucose dehydrogenase. Similarly, other analyte-specific enzyme electrode systems can detect lactate, urea, uric acid, various alcohols, and a number of amino acids under certain well-defined conditions. For example, a biosensor electrode that detects hydrogen peroxide can be used to detect ethanol using an alcohol oxidase enzyme system, alcohol with alcohol dehydrogenase enzymes, or similarly uric acid with urate oxidase system, cholesterol with a cholesterol oxidase system, theophylline with a xanthine oxidase system, and diabetic ketoacidosis (DKA) with a beta-hydroxybutyrate-dehydrogenase enzyme system.

Analytes can be detected by the sensors in the biosensors of the described devices based on their physico-chemical characteristics (spectral, optical, thermal, electromagnetic, etc.). Infrared spectroscopy measures the infrared light (0.7-25 µm) absorbed by the analyte at various wavelengths. Absorption of light is a characteristic unique to a particular molecule/analyte. For example, glucose absorbs at multiple frequencies in both the mid- and near-infrared range. If necessary, in order to achieve better sensitivity, precision, accuracy, and reliability, more than one spectral peaks or intensities over a wide spectral range can be evaluated. When analyzing for an analyte in a sample, measurements can be made in at least two different ways: by measuring light transmitted through the sample, or by measuring light reflected or remitted from the sample. The light may be transmitted via the VCSEL 370 and the photo-detector 372 in FIG. 3. In various embodiments, the sensor may perform infrared spectroscopic measurements. Other analytes suitable for spectroscopic measurement include but are limited to total bilirubin, pH, blood gasses, e.g., $PO_2$ and $PCO_2$, and other blood analytes including electrolytes and metabolites. Total hemoglobin concentration (tHb), and hemoglobin fractions e.g., oxyhemoglobin ($O_2Hb$), methemoglobin (MetHb), carboxyhemoglobin (COHb), sulfhemoglobin (SHb), and deoxyhemoglobin (HHb). Blood hemoglobin and hemoglobin fractions absorb visible light within the wavelength range of 450-700 nm. Normal oxygenated blood spectrum has two main peak wavelengths at 542 and 578 nm and absorbance rapidly decreases close to zero at wavelengths greater than 610 nm.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. An implantable biocompatible biosensor comprising:
a chip layer including a plurality of holes fabricated vertically there through;
a power source;
one or more sensors on the chip layer and coupled to the power source; and
a hydrogel matrix including one or more angiogenesis stimulating factors in contact with the chip layer, the stimulating factors causing growth of organic material through the plurality of holes when the biosensor is implanted in a subject.

2. The biosensor of claim 1, wherein the one or more sensors include a photo diode and a laser diode configured for emitting light through the grown organic material to the photo diode.

3. The biosensor of claim 1, wherein each of the holes are 20-50 μm in diameter.

4. The biosensor of claim 3, wherein the spacing between each of the holes is the same as the diameter of the holes.

5. The biosensor of claim 1, further comprising:
a second chip layer including a second plurality of holes fabricated vertically through the second chip layer, the second chip layer located over the chip layer, the second plurality of holes in alignment with the plurality of holes; and
one or more sensors on the second chip layer and coupled to the power source; and wherein the hydrogel matrix extends between the chip layer and the second chip layer.

6. The biosensor of claim 5, wherein the hydrogel matrix fills the first and second plurality of holes.

7. An implantable biocompatible biosensor comprising:
a first chip layer having a vertical hole between a top surface and a bottom surface;
a power source;
one or more sensors fabricated on the top surface;
a channel fabricated perpendicular to the vertical hole on the bottom surface; and
a hydrogel matrix having one or more angiogenesis stimulating factors filling the hole and the channel, the hydrogel matrix stimulating growth of organic material when the biosensor is implanted in a subject.

8. The biosensor of claims 1 or 7, further comprising a transmitter in communication with the one or more sensors, the one or more sensors each emitting a signal representative of a sensed characteristic of the grown organic material, the transmitter converting the signals from the one or more sensors into a digital signal representative of a sensed characteristic.

9. The biosensor of claims 1, wherein the power source is a photovoltaic cell.

10. The biosensor of claims 1 or 7, wherein the hydrogel matrix is bovine serum albumin-based, agarose-based, PEG-based, polyethylene oxide (PEO)-based, polyvinyl alcohol (PVA)-based, polyacrylic acid (PAA)-based, poly propylene furmarate-co-ethylene glycol (P(PF-co-EG))-based, alginate-based, chitosan-based, collagen-based, fibrin-based, gelatin-based, hyaluronic acid (HA)-based, poly 2-hydroxyethyl methacrylate (PHEMA)-based, poly carboxybetaine methacrylate (PCBMA)-based or a combination thereof.

11. The biosensor of claims 1 or 7, wherein the one or more sensors are any one or more of an electrode, nanoelectromechanical sensors, optical resonators, micro/nanoscale field effect transistor or a combination thereof.

12. The biosensor of claims 1 or 7, wherein the one or more angiogenesis stimulating factors induce formation of arterioles and capillaries when implanted into the subject.

13. The biosensor of claim 12, wherein the arterioles and capillaries form through the matrix in the holes in the chip.

14. The biosensor of claim 13, wherein the matrix absorbs analytes that diffuse through the arterioles and capillaries and the one or more sensors are configured to detect the analytes absorbed in the matrix.

15. The biosensor of claim 14, wherein the analytes are any one or more of proteins, ions, metabolites, gases or a combination thereof present in the blood.

16. The biosensor of claim 14, wherein the matrix further comprises agents that react with the analytes absorbed from the arterioles and capillaries into the matrix.

17. The biosensor of claims 1 or 7, wherein the angiogenesis stimulating factors is any one or more of vascular endothelial growth factor (VEGF), fibroblast growth factor (FGF)-1, FGF-2, platelet derived growth factor (PDGF), transforming growth factor (TGF)-β, angiopoietins, matrix metalloproteinase (MMP) or a variant, mutant or peptidomimetic thereof, or a combination thereof.

18. The biosensor of claim 7, further comprising a second chip layer having a hole in alignment with the hole of the first chip layer, wherein the second chip layer includes a laser diode and a photo-detector, the second chip layer located under the first chip layer and the hydrogel matrix filing the space between the first and second chip layers.

19. The biosensor of claims 2 or 18, wherein the laser diode is any one or more of double heterostructure lasers, quantum well lasers, quantum cascade lasers, separate confinement heterostructure lasers, distributed feedback lasers, vertical cavity surface emitting lasers (VCSELs), vertical external cavity surface emitting lasers (VECSELs) or external-cavity diode lasers.

20. The biosensor of claim 7, further comprising a transmitter in communication with the one or more sensors, the one or more sensors each emitting a signal representative of a sensed characteristic of the grown organic material, the transmitter converting the signals from the one or more sensors into a digital signal representative of a sensed characteristic.

21. The biosensor of claim 7, further comprising a microspectrometer for on-chip analysis of the analyte.

22. The biosensor of claim 7, wherein the matrix absorbs analytes that diffuse through the arterioles and capillaries and the one or more sensors are configured to detect the analytes absorbed in the matrix.

23. The biosensor of claim 7, wherein the matrix further comprises agents that react with the analytes from the arterioles and capillaries into the matrix.

24. The biosensor of claim 1 or 7, wherein the biosensor is configured to be implanted in the earlobe, areolar layer of the skin or within the dermis layer of the nail bed.

* * * * *